(12) United States Patent
Hayes

(10) Patent No.: US 10,934,454 B2
(45) Date of Patent: Mar. 2, 2021

(54) COATING COMPOSITION FOR A METAL SUBSTRATE

(71) Applicant: Amazon Technologies, Inc., Seattle, WA (US)

(72) Inventor: Robert Andrew Hayes, Hong Kong (CN)

(73) Assignee: Amazon Technologies, Inc., Seattle, WA (US)

( * ) Notice: Subject to any disclaimer, the term of this patent is extended or adjusted under 35 U.S.C. 154(b) by 144 days.

(21) Appl. No.: 16/254,312

(22) Filed: Jan. 22, 2019

(65) Prior Publication Data
US 2020/0231839 A1    Jul. 23, 2020

(51) Int. Cl.
| | | |
|---|---|---|
| C09D 171/02 | (2006.01) | |
| C09D 5/08 | (2006.01) | |
| C23C 14/12 | (2006.01) | |
| B05D 7/14 | (2006.01) | |

(52) U.S. Cl.
CPC .......... C09D 171/02 (2013.01); C09D 5/086 (2013.01); B05D 7/14 (2013.01); C23C 14/12 (2013.01)

(58) Field of Classification Search
CPC ...... B05D 7/14; C07C 323/12; C08G 65/007; C08G 65/3342; C09D 5/086; C09D 171/00; C09D 171/02; C23C 14/12; C23C 14/24
See application file for complete search history.

(56) References Cited

U.S. PATENT DOCUMENTS

| | | | |
|---|---|---|---|
| 2006/0054053 A1* | 3/2006 | Masutani | C09D 183/10 106/2 |
| 2006/0229218 A1 | 10/2006 | Meo et al. | |
| 2011/0226733 A1* | 9/2011 | Zu | C08F 2/38 216/37 |
| 2012/0247355 A1 | 10/2012 | Berniard et al. | |
| 2014/0000476 A1 | 1/2014 | Portet et al. | |

FOREIGN PATENT DOCUMENTS

| | | |
|---|---|---|
| EP | 2527348 A2 | 11/2012 |
| JP | 2000016968 A | 1/2000 |

OTHER PUBLICATIONS

Tamao et al.: "Hydrogen Peroxide Oxidation of the Silicon-Carbon Bond in Organoalkoxysilanes", Organometallics 1983, 2, 1694-1696.
Tonelli et al.: "Perfluoropolyether functional oligomers: unusual reactivity in organic chemistry"; Journal of Fluorine Chemistry, 118 (2002), 107-121.
Daikin Optool brochure, Oct. 2018.
International Search Report and Written Opinion dated Apr. 22, 2020 for PCT Application No. PCT/US2020/013814.

* cited by examiner

Primary Examiner — Ramsey Zacharia
(74) Attorney, Agent, or Firm — EIP US LLP

(57) ABSTRACT

A composition comprising a compound having the general formula (I):

$$F-[CF_2]_n-(O[CF_2]_n)_m-(L)_p-SH \qquad \text{(Formula (I))}$$

Each n is independently from 2 to 4, m is from 3 to 30, p is 0 or 1 and L represents a linker having the formula $O_q(CF_2)_r(CH_2)_s$, wherein q is 0 or 1, r is from 0 to 4 and s is from 0 to 4.

18 Claims, 3 Drawing Sheets

COATING COMPOSITION FOR A METAL SUBSTRATE

BACKGROUND

Portable electronic devices may have housings comprising a metal. A surface of such a metal is often vulnerable to abrasion and other damage in use, such as corrosion. It is desirable to protect metal surfaces from abrasion and other damage.

DETAILED DESCRIPTION

Figure 1A:
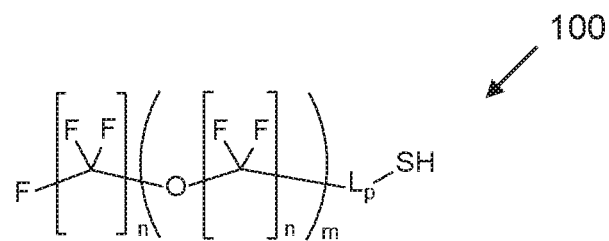
FIG. 1A illustrates a compound having a general Formula (I)

The compositions of examples described herein comprise a compound having the general formula (I):

F—[CF$_2$]$_n$—(O[CF$_2$]$_n$)$_m$-(L)$_p$-SH   (Formula (I))

Each n is an integer independently with a value in the range from 2 to 4. m is an integer with a value in the range from 3 to 30. p is 0 or 1 and L represents a linker having the formula O$_q$(CF$_2$)$_r$(CH$_2$)$_s$; q is 0 or 1, r is from 0 to 4 and s is from 0 to 4. Such a compound with the general formula (I) may otherwise be referred to as a perfluoropolyetherthiol compound.

A composition with such a compound has been found to be useful in protecting a metal substrate, for example from abrasion. With a metal substrate coated at least partially with a coating comprising a compound of formula (I), for example comprising a composition of different compounds of formula (I), a surface of the metal substrate can be less prone to damage by for example abrasion or corrosion from an external environment. It is believed, but should not be taken as limiting herein, that this protection against damage is because the coating provides a surface of lower surface energy which can help for example to repel, resist, deflect or reduce adhesion of materials or objects which might otherwise damage a surface of the metal substrate when they come into contact. Such materials may include at least one of moisture, air, or sweat from contact with a user's skin (such as a finger-tip).

Examples will now be described in further detail.

Within each compound in a composition, the value of n in each [CF$_2$]$_n$ unit may be the same. Or in other examples, the value of n in one [CF$_2$]$_n$ unit may be different from the value of n in at least one other [CF$_2$]$_n$ unit; thus, each compound may comprise a mixture of more than one of perfluoroethylene, perfluoropropylene, or perfluorobutylene units. When the value of n in each [CF$_2$]$_n$ unit is the same, when n is 2 each compound comprises solely perfluoroethylene units; when n is 3 each compound comprises solely perfluoropropylene units; and when n is 4 each compound comprises solely perfluorobutylene units.

In some examples, the value of n in each [CF$_2$]$_n$ unit is the same and n is 3, so that each compound comprises perfluoropropylene units.

Within each compound in a composition, m is from 3 to 30. In some examples, m is from 6 to 10. The value of m influences the length of the perfluoroether, and thus for example the thickness of a protective layer over a metal substrate. In some examples, the value of m may provide a layer thickness in the range of from 10 to 15 nanometres (nm).

L represents a linker, which may be present in the compound. Thus, when p is 1, this linker is present. When p is 0, this linker is absent and therefore a terminal (O[CF$_2$]$_n$) group is linked to the SH group by a single bond. The linker, when present, is represented by the formula O$_q$(CF$_2$)$_r$(CH$_2$)$_s$; q is 0 or 1, r is from 0 to 4 and s is from 0 to 4.

In some examples, q is 1, r is 1 or 2 and s is 1 or 2. In some examples, the linker has a formula selected from —OCF$_2$CF$_2$CH$_2$CH$_2$—, —OCF$_2$CF$_2$CH$_2$—, —OCF$_2$CH$_2$CH$_2$—, —OCH$_2$CH$_2$CH$_2$—, —OCF$_2$CH$_2$—, or —OCH$_2$CH$_2$—.

Figure 1B:
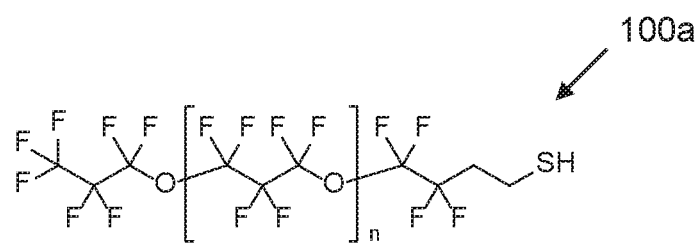
FIGS. 1B and 1C illustrate specific examples of compounds according to Formula (I)
Figure 1C:
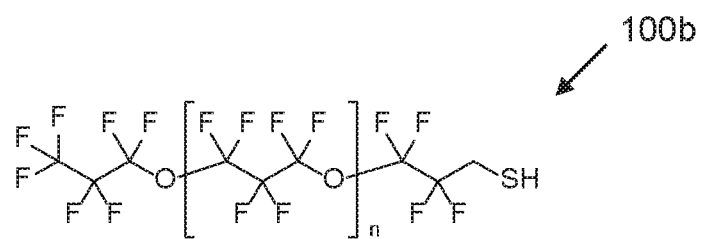

FIG. 1A shows Formula (I) graphically as compound 100; FIGS. 1B and 1C show specific compounds 100a and 100b which are examples of compounds having the formula of Formula (I).

Figure 2:
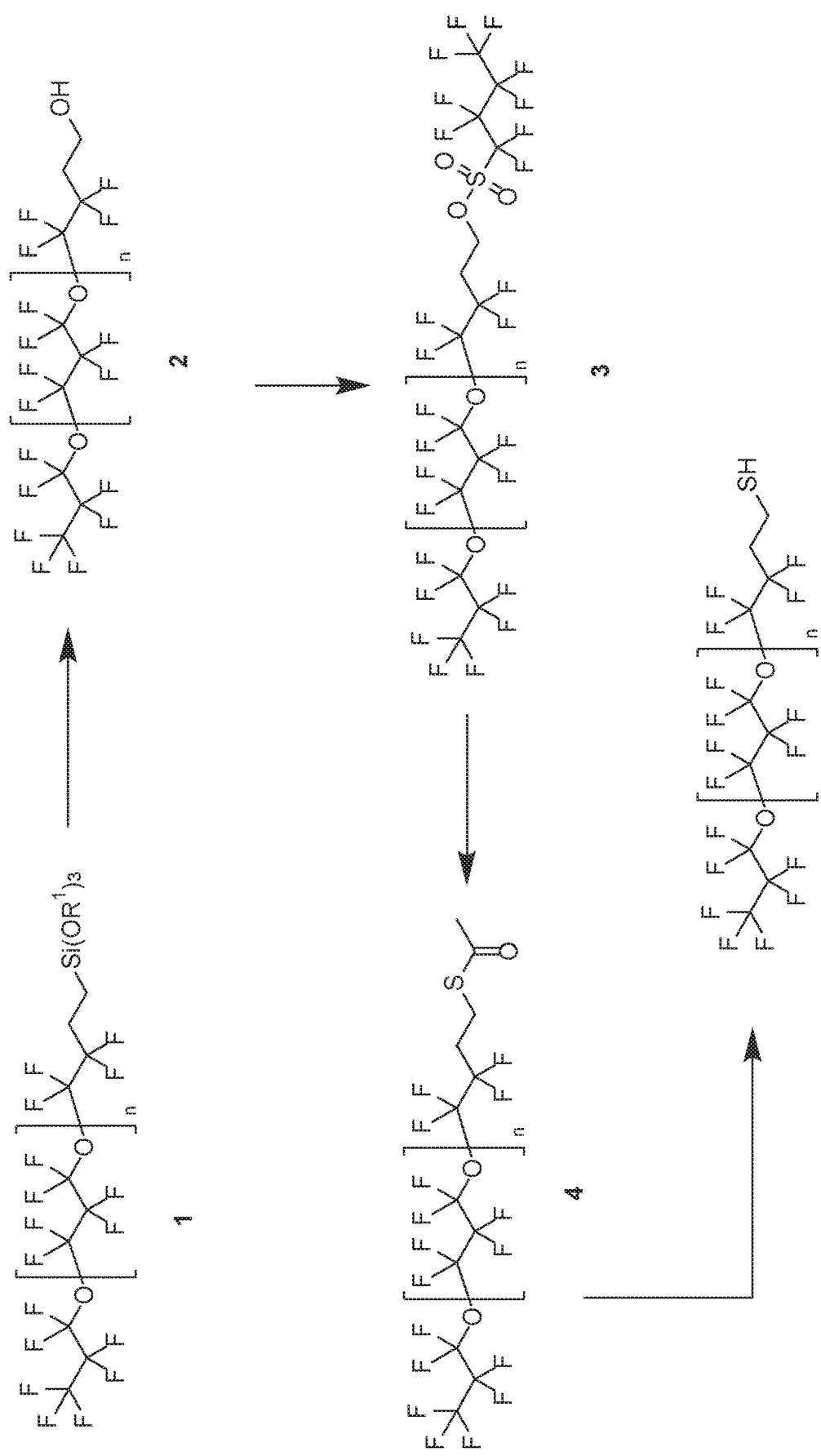
FIG. 2 illustrates an example reaction scheme for providing the compound shown in FIG. 1B.

In general, the compounds of the present disclosure may be prepared from corresponding perfluoropolyether alcohols (such as the perfluoropolyether alcohol shown as compound 2 in FIG. 2).

The perfluoropolyether alcohol may be provided by any suitable means. In examples, the perfluoropolyether alcohol may be prepared from a corresponding perfluoropolyether trialkoxysilane (such as the perfluoropolyether trialkoxysilane shown as compound 1 in FIG. 2). A suitable perfluoropolyether trialkoxysilane may be hydrolysed in the presence of hydrogen peroxide to provide the perfluoropolyether alcohol (e.g. a Tamao oxidation—see Tamao et al., *Organometallics* 1983, 2, 1694-1696).

In other examples, the perfluoropolyether alcohol may be prepared from a corresponding perfluoropolyether carboxylic acid (such as the perfluoropolyether carboxylic acid shown as compound 6 described below). A suitable perfluoropolyether carboxylic acid may be reduced (e.g. in the presence of LiAlH$_4$) to provide the perfluoropolyether alcohol.

In other examples, the perfluoropolyether alcohol may be obtained from a vendor directly without need for conversion from a precursor compound.

The perfluoropolyether alcohol can then be modified to improve the leaving group capability of the terminal alcohol moiety. For example, the alcohol may be treated with tosyl chloride (which may also be referred to as 4-toluenesulfonyl chloride, CH$_3$C$_6$H$_4$SO$_2$Cl), nosyl chloride (which may also be referred to as 4-nitrobenzenesulfonyl chloride, O$_2$NC$_6$H$_4$SO$_2$Cl) or nonafluorobutanesulfonyl fluoride (which may also be referred to as perfluorobutanesulfonyl fluoride, C$_4$F$_{10}$SO$_2$F) to provide a perfluoropolyether sulfonate ester. Such a sulfonate ester is vulnerable to nucleophilic substitution and may be treated with a reagent which provides a sulfur moiety with an oxidation state of +2 (that is required for a thiol) at the terminal position. For example, the sulfonate ester may be treated with H$_2$S to substitute the sulfonate ester moiety for a thiol moiety. However, it may be preferred not to use H$_2$S due to the difficulties of handling the reagent. Instead, it may be preferred to first treat the sulfonate ester with a thiocarboxylate to provide a perfluoropolyetherthioester, and then hydrolyse the perfluoropolyether thioester to provide a perfluoropolyetherthiol. For example, the perfluoropolyether sulfonate ester may be treated with potassium thioacetate to substitute the sulfonate ester moiety with a thioester moiety, and then hydrolyse the thioester under basic or acidic conditions to provide a perfluoropolyetherthiol of the present disclosure. Suitable conditions for such reactions can be found in Tonelli et al., Journal of Fluorine Chemistry, 118 (2002), 107-121.

In a specific example, the perfluoropolyetherthiol 100a shown in FIG. 1B can be prepared according to the reaction scheme shown in FIG. 2. This synthesis uses Optool UD509 (available from Daikin Industries, Ltd.) as a starting material. For simplicity, this compound may be referred to as $RCH_2Si(OR^1)_3$—see compound (1) below:

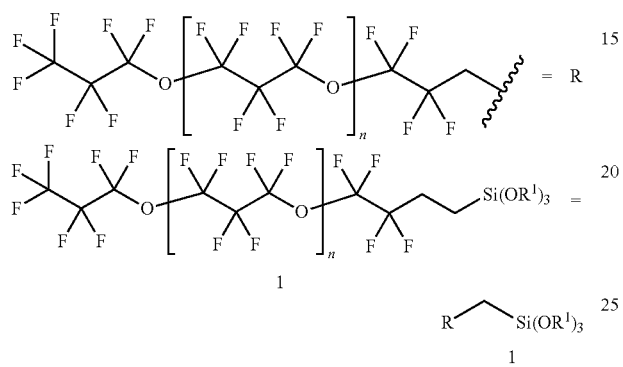

The conditions which are used in the synthesis of compound 5 according to FIG. 2 are set out in reactions labelled Reactions 1-4 below.

Reaction 1

$R\text{-}Si(OR^1)_3 \xrightarrow[\text{DMF, r.t., 3 h}]{30\% \text{ H}_2\text{O}_2 \text{ (12 e.q.), KHF}_2 \text{ (2 eq.)}} R\text{-}OH$ 1                                                      2

Optool UD509 (1), is added to potassium bifluoride (2 eq.), in DMF. To this mixture 30% $H_2O_2$ (12 eq.) is added at room temperature with stirring. After being stirred for 3 hours, the mixture is poured into water and extracted to yield $RCH_2OH$ (2).

Reaction 2

$Et_3N$ (1.1 eq.),

[perfluorobutanesulfonyl fluoride] (1.1 eq.)

$R\text{-}OH \xrightarrow[0° \text{ C., 2 h, then, r.t., 2 h}]{1,3\text{-bis(trifluoromethyl)benzene ('HFX')}}$

2

[compound 3: $RCH_2OS(O)_2C_4F_9$]

3

A mixture of $RCH_2OH$ (2) and distilled trimethylamine (1.1 eq.) is added over 2 hours at 0° C. (degrees Celsius) to a solution of perfluoro-1-butanesulfonyl fluoride (1.1 eq) in 1,3-bis(trifluoromethyl)benzene (also referred to as hexafluoroxylene, or 'HFX'). The reaction mixture is then stirred at room temperature until complete conversion of the starting alcohol is achieved (2 hours) to yield $RCH_2OS(O_2)C_4F_9$ (3).

Reaction 3

[compound 3] $\xrightarrow[\text{HFX, EtOH, 50° C., 4 h}]{CH_3C(O)SK \text{ (1.1 eq.)}}$

[compound 4: $R\text{-}CH_2\text{-}S\text{-}C(O)CH_3$]

4

A mixture of $RCH_2OS(O_2)C_4F_9$ (3), potassium thioacetate (1.1 eq.), ethanol and HFX is stirred for 4 hours at 50° C. under a nitrogen atmosphere. The reaction mixture is then acidified with dilute HCl, washed twice with water, and the solvents distilled off to give $RCH_2SC(O)CH_3$ (4).

Reaction 4

[compound 4] $\xrightarrow{\substack{1) \text{ NH}_3, \text{MeOH, HFX, r.t., 2 h} \\ 2) \text{ aq. HCl, Galden® D100}}}$

[compound 5: perfluoropolyether-SH]

5

A solution of $RCH_2SC(O)CH_3$ (4) in HFX is added drop-wise over 2 hours to methanolic ammonia (8%) at room temperature under a nitrogen atmosphere. After evaporation of the solvent and excess ammonia, the crude product is dissolved in Galden® D 100 (1:1 mixture of perfluorobutyl(tetrahydrofuran) and perfluoro-propyl(tetrahydropyran)) and washed with diluted HCl. The D 100 is distilled off to yield $RCH_2SH$ (5), the compound shown as compound 100a in FIG. 1B.

In another specific example, the perfluoropolyetherthiol 100b shown in FIG. 1C can be prepared according to the reactions labelled Reactions 5-8 below. This synthesis may use the carboxylic acid precursor Demnum SH (available from Daikin Industries, Ltd.) as a starting material. For simplicity, this compound may be referred to as RCOOH—see compound (6) below:

-continued

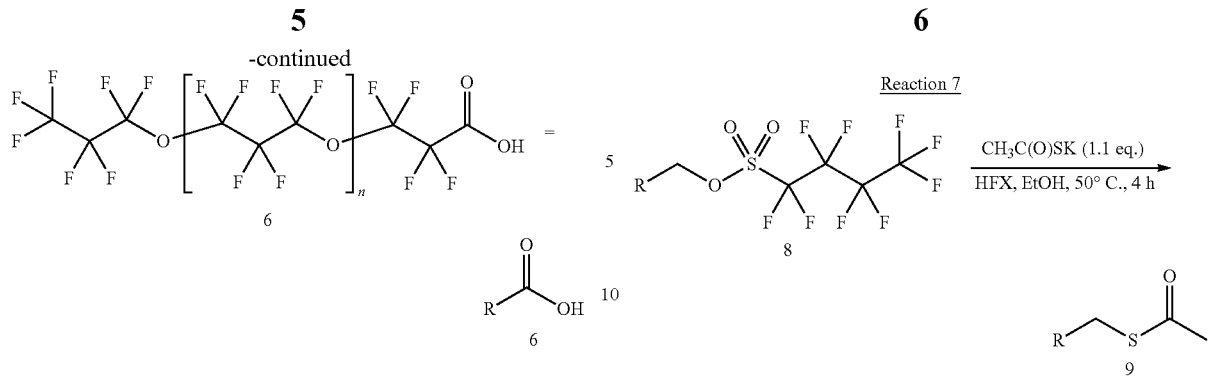

Reaction 5 includes reducing the perfluoropolyether alcohol; Reactions 6-8 broadly correspond to Reactions 2-4.

Reaction 5

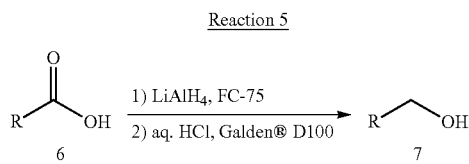

LiAlH$_4$ in perfluoro-2-n-butyl THF (also referred to as "FC-75") is charged to a flask under nitrogen. A solution of RCOOH (6) in FC-75 is added dropwise to the flask, and the mixture stirred under a nitrogen atmosphere. The reaction mixture is cooled, and dilute aqueous HCl is added dropwise to quench the reaction. The mixture is then washed with further dilute aqueous HCl, and the FC-75 distilled off to yield RCH$_2$OH (7).

In the synthesis of perfluoropolyetherthiol 100b, Reaction 5 may be used in some examples, but in other examples may not be used. That is, rather than carrying out Reaction 5, compound (7) may be obtained directly from Daikin Industries, Ltd. as Demnum SA and used as the starting material from Reaction 6 onwards.

Reaction 6

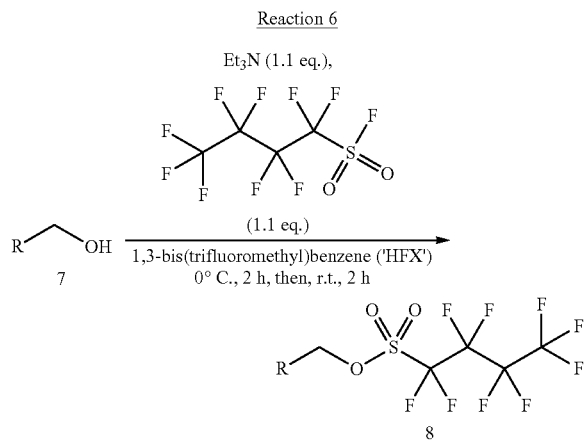

A mixture of RCH$_2$OH (7) and distilled trimethylamine (1.1 eq.) is added over 2 hours at 0° C. (degrees Celsius) to a solution of perfluoro-1-butanesulfonyl fluoride (1.1 eq) in HFX. The reaction mixture is then stirred at room temperature until complete conversion of the starting alcohol is achieved (2 hours) to yield RCH$_2$OS(O$_2$)C$_4$F$_9$ (8).

Reaction 7

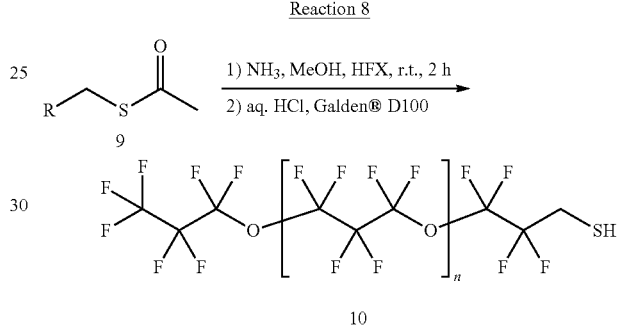

A mixture of RCH$_2$OS(O$_2$)C$_4$F$_9$ (8), potassium thioacetate (1.1 eq.), ethanol and HFX is stirred for 4 hours at 50° C. under a nitrogen atmosphere. The reaction mixture is then acidified with dilute HCl, washed twice with water, and the solvents distilled off to give RCH$_2$SC(O)CH$_3$ (9).

Reaction 8

A solution of RCH$_2$SC(O)CH$_3$ (9) in HFX is added drop-wise over 2 hours to methanolic ammonia (8%) at room temperature under a nitrogen atmosphere. After evaporation of the solvent and excess ammonia, the crude product is dissolved in Galden® D 100 and perfluoro-propyl(tetrahydropyran) and washed with diluted HCl. The D 100 is distilled off to yield RCH$_2$SH (10), the compound shown as compound 100b in FIG. 1C.

A composition of the present disclosure may contain a plurality of different compounds each having the general formula (I), for example a first compound and a second compound each in accordance with the general formula (I). Alternatively, the compositions may comprise substantially a single compound having the general formula (I), so that m, n, p and L are the same for substantially all compounds having the general formula (I) within the composition. The degree to which a composition comprising substantially a single compound having the general formula (I) can be achieved is limited by the purity of available starting materials, the synthetic routes used to make the compositions, and the degree of purification that can be achieved. In examples, over 50%, over 60%, over 70%, over 80%, over 90%, or over 95% of the compounds having the general formula (I) within the composition may be the same compound.

The compositions may be applied, for example coated, onto a surface of a metal substrate so that the surface is at least partially coated. In some examples most or all of the surface that is exposed to the external environment may be coated. Or, in other examples a portion of the surface may be left uncoated. Typically, a coating used herein refers to a layer or intermediate material between a surface of a metal substrate and an external environment. This may protect the metal surface from interaction with the external environment, such as from interaction with at least one of moisture, the air, or sweat. A coated portion of the metal substrate may be considered to be covered or overlapped by a material, in this case a compound or compounds described in examples herein. In some examples the coating may act as a barrier to the external environment reaching the metal substrate surface; this may be a partial barrier which partially reduces exposure of the metal substrate surface to the external environment, or a complete barrier which blocks exposure of the surface to the external environment.

In some examples, the thiol group present in the compounds interacts with the metal of the metal substrate in order to adhere the compound to the metal surface. This interaction may have the character of a chemical bond, or it may be a weaker interaction.

Figure 3:
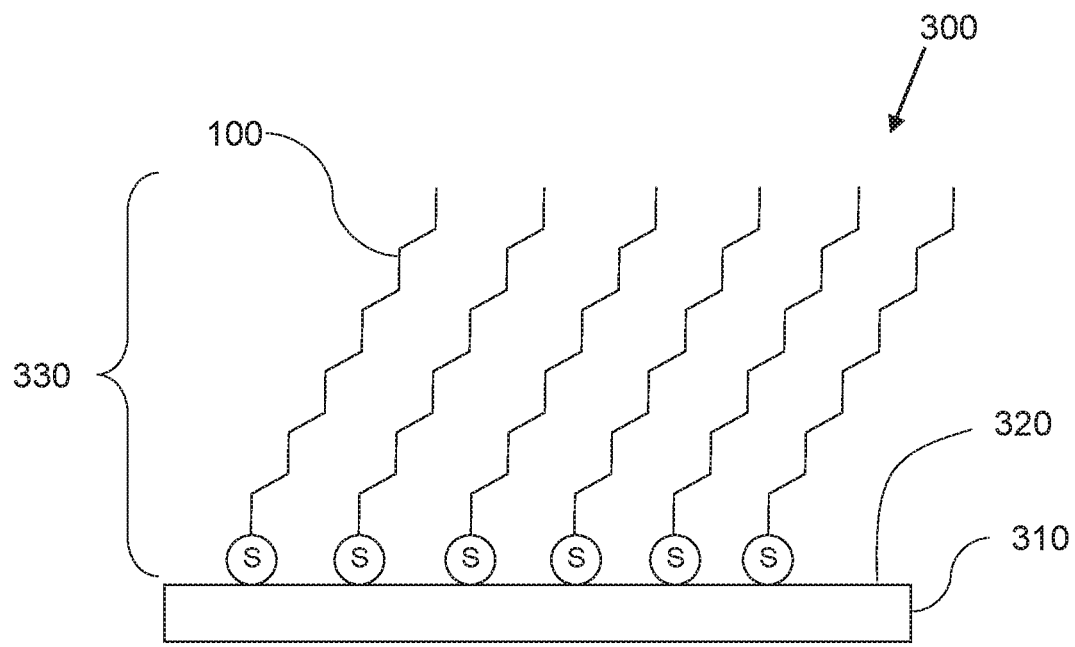
FIG. 3 illustrates a coated metal substrate according to examples.

In some examples, it is envisaged that a composition coated onto a surface of a metal substrate forms a layer of the compounds over the metal substrate, with the thiol groups bound to the metal surface, and the perfluoropolyether portions aligning with each other to form part of a layer. This is depicted schematically in FIG. 3, which shows coated metal substrate 300 comprising a metal substrate 310 having a surface 320. A layer 330 is provided on the surface, the layer 330 comprising compounds 100 of Formula (I), with the compounds 100 bound to the surface 320 with the S of thiol groups.

The metal substrate is typically in examples an amount of material which comprises metal atoms. The metal substrate may comprise metal in elemental form, or may comprise a metal compound, such as an oxide, or may comprise both metal in elemental form and a metal compound, such as an oxide. The metal substrate may comprise at least one of gold, silver, copper, silver oxide, or copper oxide. In some examples, the metal substrate may comprise gold. In some other examples, the metal substrate may comprise silver, silver oxide, or a mixture of silver and silver oxide. In some examples, the metal substrate may comprise copper, copper oxide, or a mixture of copper and copper oxide. In some examples the metal substrate may be an alloy comprising at least one of gold, silver, and copper. In some examples, the metal substrate may comprise a metal that forms a strong association with sulfur. In some examples, the metal substrate may comprise a metal that can react with elemental sulfur to form a corresponding metal sulfide at least to some extent at a temperature below 120° C.

The metal substrate may have a form or shape for assembly as part of a particular electronic device. The metal substrate may therefore be part of a component for a device, such as a portable device, such as a portable electronic device, which may be used in outdoor environments. For example, the metal substrate may be part or all of a housing, frame, bezel, casing, or other component for a portable device such as a portable electronic device. Typically, a portable device is a device capable of being moved or carried under normal, for example without undue effort, by a human Such a portable device may be a device wearable by a user, in other words a wearable device, such as a watch, a ring, a fitness band, or another device capable of being attached to or worn by a user.

Figure 4:
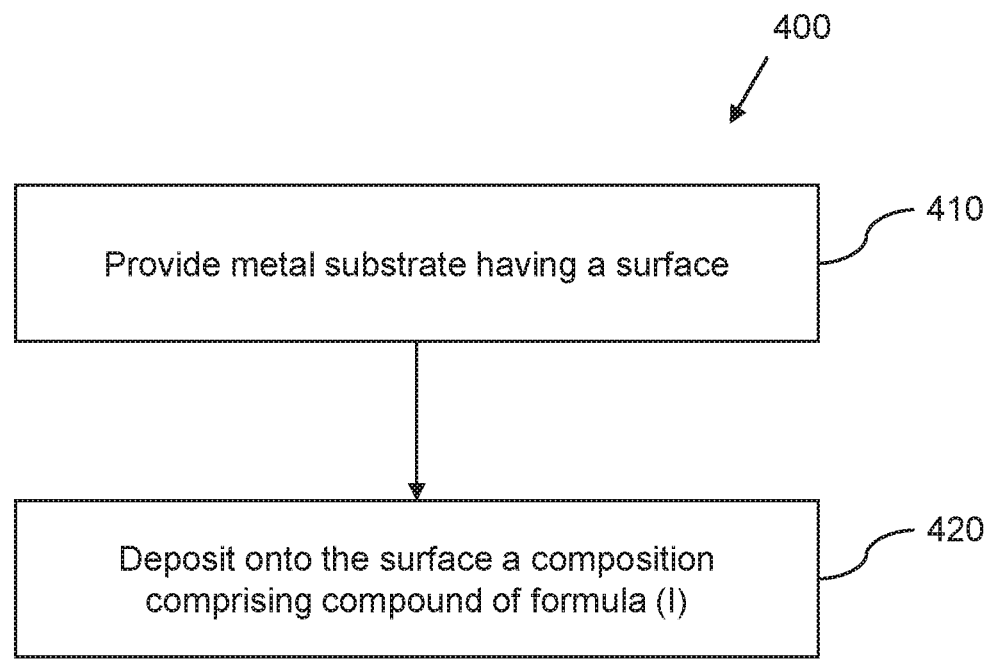
FIG. 4 illustrates a method of coating a metal substrate with a composition according to examples.

An example method of forming a coating on the metal substrate is described in FIG. 4. The method 400 comprises providing a surface of a metal substrate 410, then depositing a composition comprising a compound of formula (I) on the surface of the metal substrate 420.

In order to form a coating onto a metal substrate, vapour deposition or solution deposition may be employed to deposit the composition on the surface.

For vapour deposition, the composition may be deposited substantially neat, thus substantially no solvent or diluent is present. A substantially neat composition may comprise over 80%, over 90%, or over 95% by weight of compounds having the general formula (I). The deposition may be carried out in an evacuated system (therefore at least in some examples substantially under vacuum).

For solution deposition, the composition may further comprise a diluent. Suitable diluents are known to the person skilled in the art and may be, for example, a perfluoroalkane such as perfluorohexane or perfluoroheptane, and/or a hydrofluoroalkane such as 2H,3H-perfluoropentane (also referred to as Vextrel® XF) and/or a hydrofluoroether such as methoxy-nonafluorobutane (also referred to as 3M® Novec® 7100) or ethoxy-nonafluorobutane (also referred to as 3M® Novec® 7200) and/or a perfluoropolyether such as $F-[CF(CF_3)-CF_2-O]_n-CF_2CF_3$ (also referred to as Krytox® GLM 105).

The compound of formula (I) may have any suitable concentration in the solution. In some examples, the compound of formula (I) may be present in the solution in a concentration of from about 0.01 to 1.0 wt %, or from about 0.05 to 0.5 wt %, or about 0.1 wt %.

Before depositing the composition via vapour deposition or solution deposition, the surface of the metal substrate may be cleaned. For example, the surface may be cleaned by plasma cleaning. This may improve the adhesion of the thiol to the metal substrate.

The solution comprising a compound of formula (I) may be deposited in any suitable thickness. For example, the solution may be deposited in a thickness of from about 1 to 50 micro-metres ($\mu$m), or from about 5 to 20 $\mu$m, or about 10 $\mu$m.

The solution may be deposited on the surface by any suitable method. For example, the solution may be deposited by dip coating, spin coating, spray coating, screen printing In some examples, after the deposition the coated metal substrate may be heated, and this may strengthen the interaction between the thiol and the metal substrate and/or remove solvent from the deposited composition. In some examples the coated metal substrate may be heated to a temperature greater than room temperature, or greater than about 30° C., or greater than about 50° C., or greater than about 80° C., or greater than about 100° C., or greater than about 120° C. In some examples the coated metal substrate may be heated to a temperature less than about 150° C., or less than about 120° C., or less than about 100° C. In some examples the coated metal substrate may be heated to a temperature of from about 30° C. to 200° C., or from about 50° C. to 150° C., or from about 80° C. to 120° C.

Further examples are envisaged, which include combinations of features of the originally filed claims, as indicated in the following table, which lists various envisaged claim dependencies for the claims originally filed with this application. Hence, in addition to the description above, this table gives basis in the specification for general examples having a combination of features of claims filed herewith:

| Claim as Originally Filed | Envisaged Claim Dependencies |
|---|---|
| 1 | — |
| 2 | 1 |
| 3 | 2 |

-continued

| Claim as Originally Filed | Envisaged Claim Dependencies |
|---|---|
| 4 | Any one of claims 1 to 3 |
| 5 | Any one of claims 1 to 4 |
| 6 | Any one of claims 1 to 4 |
| 7 | Any one of claims 1 to 4 |
| 8 | Any one of claims 1 to 7 |
| 9 | Any one of claims 1 to 7 |
| 10 | Any one of claims 1 to 9 |
| 11 | Any one of claims 1 to 9 |
| 12 | 11 |
| 13 | — |
| 14 | 13 |
| 15 | 13, 14 |
| 16 | Any one of claims 13 to 15 |
| 17 | Any one of claims 13 to 15 |
| 18 | — |
| 19 | 18 |
| 20 | 18 |

It is to be understood that any feature described in relation to any one example may be used alone, or in combination with other features described, and may also be used in combination with one or more features of any other of the examples, or any combination of any other of the examples. Furthermore, equivalents and modifications not described above may also be employed without departing from the scope of the accompanying claims.

What is claimed is:

1. A metal substrate which is at least a part of a housing, frame, bezel or casing for a portable electronic device, the metal substrate comprising a surface exposed to an external environment during use of the portable electronic device, wherein at least a portion of the surface comprises a layer of a compound having the general formula (I):

$$F\text{—}[CF_2]_n\text{—}(O[CF_2]_n)_m\text{-}(L)_p\text{-}SH \qquad \text{(Formula (I))}$$

wherein each n is independently from 2 to 4, m is from 3 to 30, p is 0 or 1 and L represents a linker having the formula $O_q(CF_2)_r(CH_2)_s$, wherein q is 0 or 1, r is from 0 to 4 and s is from 0 to 4.

2. The metal substrate according to claim 1 wherein n in each $[CF_2]_n$ unit has the same value.

3. The metal substrate according to claim 2 wherein n is 3.

4. The metal substrate according to claim 1, wherein m is from 6 to 10.

5. The metal substrate according to claim 1, wherein p is 0.

6. The metal substrate according to claim 1, wherein p is 1, q is 1, r is 1 or 2 and s is 1 or 2.

7. The metal substrate according to claim 1, wherein p is 1 and L has a formula selected from —OCF$_2$CF$_2$CH$_2$CH$_2$—, —OCF$_2$CF$_2$CH$_2$—, —OCF$_2$CH$_2$CH$_2$—, —OCH$_2$CH$_2$CH$_2$—, —OCF$_2$CH$_2$—, or —OCH$_2$CH$_2$—.

8. The metal substrate according to claim 1, wherein the layer comprises substantially a single compound having the general formula (I).

9. The metal substrate according to claim 1, wherein the layer comprises a plurality of different compounds having the general formula (I).

10. The metal substrate according to claim 1, wherein the metal substrate comprises at least one of gold, silver, copper, silver oxide, or copper oxide.

11. A method comprising:
providing a metal substrate having a surface;
depositing onto the surface a composition comprising a compound having the general formula (I):

$$F\text{—}[CF_2]_n\text{—}(O[CF_2]_n)_m\text{-}(L)_p\text{-}SH \qquad \text{(Formula (I))}$$

wherein each n is independently from 2 to 4, m is from 3 to 30, p is 0 or 1 and L represents a linker having the formula $O_q(CF_2)_r(CH_2)_s$, wherein q is 0 or 1, r is from 0 to 4 and s is from 0 to 4; and
wherein the metal substrate is for part of a portable electronic device with the surface exposed to an external environment of the portable electronic device.

12. A method according to claim 11, wherein the composition is substantially neat and depositing comprises a vapour deposition process.

13. A method according to claim 11, wherein the composition further comprises a diluent and depositing comprises a solution deposition process.

14. The method according to claim 13, wherein the diluent is a perfluoroalkane, a hydrofluoroalkane, a hydrofluoroether, or a mixture thereof.

15. A method according to claim 11, wherein substantially all of the surface for exposure to the external environment comprises a layer of the compound.

16. A portable electronic device comprising at least one of a housing, frame, bezel, or casing, the at least one housing, frame, bezel, or casing comprising a metal substrate with a surface exposed to an external environment during use of the portable electronic device, at least a portion of the surface comprising a layer of a compound having the general formula (I):

$$F\text{—}[CF_2]_n\text{—}(O[CF_2]_n)_m\text{-}(L)_p\text{-}SH \qquad \text{(Formula (I))}$$

wherein each n is independently from 2 to 4, m is from 3 to 30, p is 0 or 1 and L represents a linker having the formula $O_q(CF_2)_r(CH_2)_s$, wherein q is 0 or 1, r is from 0 to 4 and s is from 0 to 4.

17. The portable electronic device of claim 16, wherein the portable electronic device is a wearable device.

18. The portable electronic device of claim 16, wherein the portable electronic device is at least one of a watch, a ring, or a fitness band.

* * * * *

UNITED STATES PATENT AND TRADEMARK OFFICE
CERTIFICATE OF CORRECTION

PATENT NO. : 10,934,454 B2
APPLICATION NO. : 16/254312
DATED : March 2, 2021
INVENTOR(S) : Robert Andrew Hayes Page 1 of 1

It is certified that error appears in the above-identified patent and that said Letters Patent is hereby corrected as shown below:

In the Claims

Column 10, Line 23, Claim 12, delete "A method according to claim" and insert -- The method according to claim --, therefor.

Column 10, Line 26, Claim 13, delete "A method according to claim" and insert -- The method according to claim --, therefor.

Column 10, Line 32, Claim 15, delete "A method according to claim" and insert -- The method according to claim --, therefor.

Signed and Sealed this
Tenth Day of August, 2021

Drew Hirshfeld
*Performing the Functions and Duties of the*
*Under Secretary of Commerce for Intellectual Property and*
*Director of the United States Patent and Trademark Office*